(12) United States Patent
Lalleman et al.

(10) Patent No.: US 8,231,690 B2
(45) Date of Patent: Jul. 31, 2012

(54) COMPOSITION COMPRISING DERIVATIVES OF PHENOXAZINONES FOR HAIR COLOURING

(75) Inventors: Boris Lalleman, Paris (FR); Patrick Choisy, Montlouis sur Loire (FR); Alain Lagrange, Coupvray (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/129,874

(22) PCT Filed: Nov. 16, 2009

(86) PCT No.: PCT/EP2009/065235
§ 371 (c)(1),
(2), (4) Date: Aug. 5, 2011

(87) PCT Pub. No.: WO2010/057854
PCT Pub. Date: May 27, 2010

(65) Prior Publication Data
US 2011/0297172 A1    Dec. 8, 2011

Related U.S. Application Data

(60) Provisional application No. 61/116,744, filed on Nov. 21, 2008.

(30) Foreign Application Priority Data

Nov. 19, 2008    (FR) ...................... 08 57859

(51) Int. Cl.
*A61Q 5/00* (2006.01)
*C07D 265/38* (2006.01)
(52) U.S. Cl. ............. 8/405; 8/435; 8/565; 8/576; 8/607; 544/102

(58) Field of Classification Search .............. 8/405, 435, 8/565, 576, 607; 544/102
See application file for complete search history.

(56) References Cited

U.S. PATENT DOCUMENTS
2006/0230547 A1* 10/2006 Kobayashi ........................ 8/405

FOREIGN PATENT DOCUMENTS
EP          2 098 228 A1    9/2009
WO    WO-2008/047055 A2    4/2008
WO    WO-2008/047758 A1    4/2008

OTHER PUBLICATIONS

STIC Search Report dated Dec. 21, 2011.*

* cited by examiner

*Primary Examiner* — Eisa Elhilo
(74) *Attorney, Agent, or Firm* — Connolly Bove Lodge & Hutz LLP

(57) ABSTRACT

The present invention relates to a composition for the coloring of keratin fibres, notably hair, that comprises a phenoxazinone dye of formula (I) as well as the use of this dye for hair coloring. The invention thus makes it possible to obtain coloration that respects the nature of the hair and offers strong shades, which are resistant and have low selectivity.

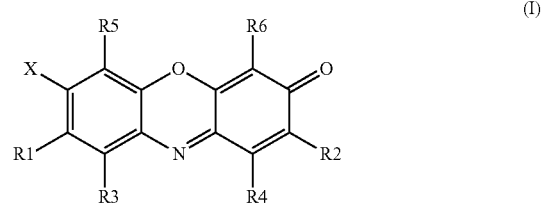

20 Claims, No Drawings

COMPOSITION COMPRISING DERIVATIVES OF PHENOXAZINONES FOR HAIR COLOURING

CROSS REFERENCE TO RELATED APPLICATIONS

This application is a National Phase filing under 35 U.S.C. §371 of PCT/EP2009/065235 filed on Nov. 16, 2009; and this application claims priority to Application No. 0857859 filed in France on Nov. 19, 2008; and claims the benefit of U.S. Provisional Application No. 61/116,744 filed Nov. 21, 2008; the entire contents of all are hereby incorporated by reference.

The invention relates to a hair colouring composition based on phenoxazinone derivatives.

Dyeing of keratin fibres and in particular human hair with dye compositions containing precursors of oxidation dyes, generally called oxidation bases, such as ortho or paraphenylenediamines, ortho or paraminophenols and heterocyclic compounds, is already known. These oxidation bases are in general combined with couplers. These bases and couplers are colourless or faintly coloured compounds which, combined with oxidizing products, can give rise to coloured compounds by a process of oxidative condensation.

This type of oxidation dyeing allows permanent dyeing to be obtained, but it causes degradation of the keratin fibres through the use of oxidizing agents.

Moreover, dyeing of keratin fibres and in particular human hair with dyeing compositions containing direct dyes is also known. The classical dyes that are used are in particular dyes of the nitrobenzene, anthraquinone, nitropyridine, azo, azo, xanthene, acridine, azine, triarylmethane type or natural dyes. These dyes can be nonionic, anionic, cationic or amphoteric. Said dyes are coloured and colouring molecules having an affinity for keratin fibres.

These compositions containing one or more direct dyes are applied on the keratin fibres for the time required to obtain the desired coloration, and then rinsed.

The resultant colouring is particularly chromatic colouring, but it is temporary or semi-permanent, as the nature of the interactions that bind the direct dyes to the keratin fibre, and their desorption from the surface and/or from the interior of the fibre are responsible for their low dyeing power and their poor resistance to washing or to sweating.

These drawbacks are even more marked when natural dyes are used.

The aim of the present invention is to provide novel compositions for the dyeing of human hair which respect the nature of the hair and offer dyeing that is powerful, of low selectivity and resistant, capable of generating strong new dyes that can give varied shades. Another aim of the invention is to make available compositions for hair colouring by means of natural dyes that are more satisfactory.

This aim is achieved with the present invention, which relates to a hair colouring composition that comprises, in a medium suitable for hair colouring containing one or more thickening agents and/or one or more surfactants, one or more dyes of formula

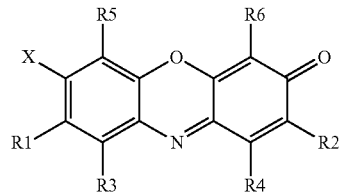

(I)

in which

X is selected from a hydrogen atom; an alkyl radical having from 1 to 10 carbon atoms and optionally substituted with one or more hydroxyl radicals; a phenyl radical optionally substituted with one or more $C_1$-$C_{10}$ hydroxyl or alkyl radicals, a hydroxyl radical, R1 is selected from a hydrogen atom; a hydroxyl radical; a benzoyl or p-hydroxybenzoyl radical; a phenyl radical optionally substituted with one or more $C_1$-$C_{10}$ hydroxyl or alkyl radicals, for example a 2,4-dihydroxyphenyl (2,4 DHP) radical of formula (II); an amino radical $NH_2$ or NHR or NRR', R and R' representing a $C_1$-$C_{10}$ alkyl or hydroxyalkyl radical, and R and R' can form, with the nitrogen atom to which they are attached, an aromatic or non-aromatic ring, for example a morpholine, pyrrole or pyridine ring,

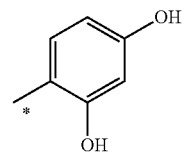

(II)

R2 is selected from a hydroxyl radical; an amino radical $NH_2$ or NHR or NRR', R and R' being as defined previously; a phenyl radical optionally substituted with one or more $C_1$-$C_{10}$ hydroxyl or alkyl radicals, notably a 2,4-dihydroxyphenyl radical (2,4 DHP) (formula (II)), R3 is selected from a hydrogen atom; a hydroxyl radical; an alkyl radical having from 1 to 10 carbon atoms and optionally substituted with one or more hydroxyl radicals; a radical COR''' or COOR''' with R''' representing a hydrogen atom, a $C_1$-$C_{10}$ alkyl radical, an amino radical $NH_2$ or NHR or NRR', R and R' being as defined previously, R4 is selected from a hydrogen atom, a $C_2$-$C_{10}$ alkenyl radical and optionally substituted with one or more hydroxyl radicals; a hydroxyl radical; a radical COOR''' or COR''' with R''' equal to hydrogen, a $C_1$-$C_{10}$ alkyl radical; an amino radical $NH_2$ or NHR or NRR', R and R' being as defined previously, R2 and R4 or R1 and R3 taken two at a time can together form an aromatic or non-aromatic, heterocyclic or carbocyclic ring with 5 or 6 ring members, R5 and R6 represent independently a hydrogen atom; a hydroxyl radical; an amino radical $NH_2$ and NHR or NRR', R and R' being as defined previously.

The invention also relates to the use of dyes of formula (I) for the colouring of keratin fibres, notably the hair, and a method of colouring the hair that comprises the application of one or more dyes of formula (I) on the fibres for a sufficient time to obtain the desired coloration.

As examples of dyes of formula (I), we may mention the following dyes:

Resorcin blue
(CAS = 71939-12-3)

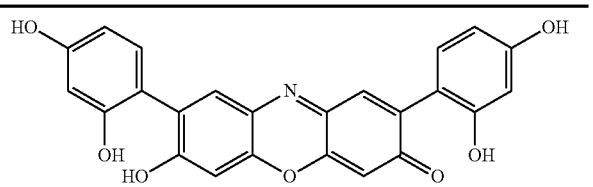

Cinnabarine acid
(CAS = 146-90-7)

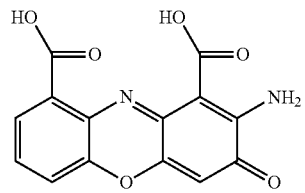

Cinnabarine
(CAS = 606-59-7)

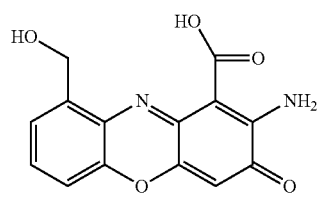

Tramsanguine
(CAS = 34083-17-5)

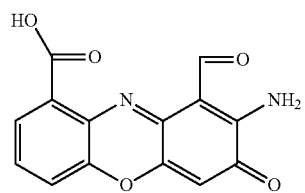

Pirenoxine sodium, CAS = 34083-17-5

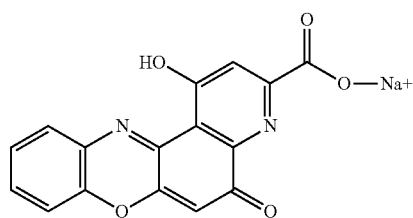

According to a particular embodiment, the alkyl radicals of the dyes of formula (I) have from 1 to 4 carbon atoms. Preferably, the dyes of formula (I) are such that R6 and R5 denote a hydrogen atom. Radical X is preferably a hydrogen atom or a hydroxyl radical.

The dyes of formula (I) are compounds already known in the prior art.

The synthesis of Resorcin blue (CAS=71939-12-3) is notably described in Chemische Berichte (1963), 96, 1579-87 and in Angewandte Chemie (1961), 73, 434-5.

Tramesanguine can be produced by the basidiomycete fungus *Pycnoporus cinnabarinus* as described in Microbiological Research (1997), 152(3), 315-318. It can also be produced by *Trametes cinnabarina* var *sanguines* as stated in Acta Chemica Scandinavica (1963), 17(3), 703-8.

Cinnabarine can be produced by the fungus *Pycnoporus sanguineus* as described in Journal of Raman Spectroscopy (2007), 38(12), 1628-1632 or Revista de microbiologia (1999), 30(1), 89 or Journal of Chemical Technology and Biotechnology (1997), 70(1), 57-59. It can also be produced by *Coriolus sanguineus* as described in Archives of Pharmacal Research (1978), 1(1), 33-40. This compound can also be obtained by synthesis as described in Tetrahedron Letters (1968), (18), 2161-6.

Cinnabarine acid can be produced by *Pycnoporus cinnabarinus* as stated in Microbiological Research (1997), 152(3), 315-318. It can also be found in the hair of certain marsupials such as *Trichosurus vulpecula* as described in Pigment Cell (1973), 1, 142-50 or International Journal of Biochemistry (1971), 2(11), 593-603. It can also be obtained by synthesis as described in Archives of Biochemistry and Biophysics (1990), 276(1), 248-50 or Journal of Organic Chemistry (1988), 53(7), 1486-8.

In fact the last three compounds are commonly produced by the various species of the genus *Pycnoporus* as described in Journal of Pharmaceutical Sciences (1971), 60 (7), 1097-8.

It is thus to be noted that certain of the phenoxazinones of the invention are of natural origin, so that it is possible to make available hair colouring compositions of natural origin.

The suitable medium for dyeing, also called dyeing aid, generally comprises water or a mixture of water and one or more organic solvents. As examples of organic solvent, we may mention the $C_1$-$C_4$ lower alkanols, such as ethanol and isopropanol; polyols and polyol ethers such as 2-butoxyethanol, propylene glycol, propylene glycol monomethyl ether, monoethyl ether and monomethyl ether of diethylene glycol, as well as aromatic alcohols such as benzyl alcohol or phenoxyethanol, and mixtures thereof; cyclic carbonates such as propylene carbonate.

The solvents are, preferably, present in proportions preferably between about 1 and 40 wt. % relative to the total weight of the dye composition, and even more preferably between about 5 and 30 wt. %.

The amount of dyes of formula (I) contained in the composition of the invention is in general between 0.001% and 20 wt. % of the total weight of the composition, preferably between 0.05 and 10%.

The compositions that can be used can also contain various additives classically used in hair dyeing compositions, such as anionic, cationic, nonionic, amphoteric, zwitterionic surfactants or mixtures thereof, anionic, nonionic, cationic, amphoteric, zwitterionic polymers or mixtures thereof, inorganic or organic thickening agents, and in particular anionic, cationic, nonionic and amphoteric associative polymeric thickeners, antioxidants, penetrating agents, sequestering agents, perfumes, buffers, dispersants, conditioners, film-forming agents, ceramides, preservatives, opacifiers.

As conditioner, we may mention the linear, cyclic, branched or unbranched, volatile or non-volatile silicones. These silicones can be in the form of oils, resins or gums, they can in particular be polyorganosiloxanes that are insoluble in the cosmetically acceptable medium.

The organopolysiloxanes are defined in more detail in the work of Walter NOLL "Chemistry and Technology of Silicones" (1968) Academic Press. They can be volatile or non-volatile.

When they are volatile, the silicones are more particularly selected from those having a boiling point between 60° C. and 260° C.

As conditioner, it is also possible to use polymers such as the polyquaterniums 22, 6, 10, 11, 35 and 37 and hexadimethrine chloride.

The concentration of conditioner(s) in the composition or compositions for use in the invention can vary from 0.01 to 10 wt. % relative to the total weight of the composition, preferably from 0.05 to 5% and even more preferably from 0.1 to 3%.

As stated above, the compositions for use in the present invention can additionally contain one or more thickening agents, also called "rheology adjusting agents".

"Thickening agent" means any compound whose presence can increase the viscosity of the medium by at least 50 cP at 25° C. at a shear rate of 1 s$^{-1}$. The viscosity can notably be evaluated by means of a cone-and-plate viscosimeter.

The thickening agents can be selected from the amides of fatty acids (copra diethanol- or monoethanol-amide, monoethanol amide of ethoxylated alkyl ether carboxylic acid), cellulosic thickeners for example nonionic of the hydroxyalkylcellulose type, for example hydroxyethylcellulose, hydroxypropylcellulose but also carboxymethylcellulose anionic celluloses, guar gum and its derivatives (hydroxypropylguar), gums of microbial origin (xanthan gum, scleroglucan gum), crosslinked homopolymers of acrylic acid or of acrylamidopropanesulphonic acid and associative polymers (water-soluble polymers comprising hydrophilic zones, and fatty-chain hydrophobic zones capable, in an aqueous medium, of associating reversibly with one another or with other molecules).

As stated above, the compositions that can be used can additionally contain one or more surfactants.

Surfactants suitable for use in the present invention are notably:

(i) Anionic Surfactant(s):

As examples of anionic surfactants that can be used, alone or as mixtures, within the scope of the present invention, we may notably mention (non-exhaustive list) the salts (in particular alkaline salts, notably of sodium, ammonium salts, salts of amines, salts of aminoalcohols or magnesium salts) of the following compounds: alkylsulphates, alkylethersulphates, alkylamidoethersulphates, alkylarylpolyethersulphates, alkylamidoethersulphates, alkylarylpolyethersulphates, monoglyceride sulphates; alkylsulphonates, alkylphosphates, alkylamidesulphonates, alkylarylsulphonates, α-olefin-sulphonates, paraffin-sulphonates; alkyl($C_6$-$C_{24}$) sulphosuccinates, alkyl($C_6$-$C_{24}$) ethersulphosuccinates, alkyl ($C_6$-$C_{24}$) amidesulphosuccinates; alkyl($C_6$-$C_{24}$) sulphoacetates; acyl($C_6$-$C_{24}$) sarcosinates and acyl($C_6$-$C_{24}$) glutamates. It is also possible to use alkyl($C_6$-$C_{24}$)polyglycoside carboxylic esters such as alkylglycoside citrates, alkylpolyglycoside tartrate and alkylpolyglycoside sulphosuccinates, alkylsulphosuccinamates; acylisethionates and N-acyltaurates, the alkyl or acyl radical of all these various compounds preferably having from 12 to 20 carbon atoms, and the aryl radical preferably denoting a phenyl or benzyl group. Among the anionic surfactants that can also be used, we may also mention the salts of fatty acids such as the salts of oleic, ricinoleic, palmitic, stearic acids, the acids of copra oil or of hydrogenated copra oil; the acyllactylates whose acyl radical has 8 to 20 carbon atoms. It is also possible to use the alkyl D galactoside uronic acids and their salts, the polyoxyalkylenated alkyl($C_6$-$C_{24}$) ether carboxylic acids, the polyoxyalkylenated alkyl($C_6$-$C_{24}$) aryl ether carboxylic acids, the polyoxyalkylenated alkyl ($C_6$-$C_{24}$) amido ether carboxylic acids and their salts, in particular those having from 2 to 50 alkylene oxide, in particular ethylene oxide, groups, and mixtures thereof.

(ii) Nonionic Surfactant(s):

The nonionic surfactants are also compounds that are well known per se (see notably in this regard "Handbook of Surfactants" by M. R. PORTER, published by Blackie & Son (Glasgow and London), 1991, pp 116-178). Thus, they can notably be selected from (non-exhaustive list) the alcohols, the alpha-diols, the polyethoxylated, polypropoxylated alkylphenols, having a fatty chain with for example 8 to 18 carbon atoms, and with the number of ethylene oxide or propylene oxide groups notably in the range from 2 to 50. We may also mention the copolymers of ethylene and propylene oxide, the condensates of ethylene and propylene oxide on fatty alcohols; the polyethoxylated fatty amides preferably having from 2 to 30 moles of ethylene oxide, the polyglycerolated fatty amides having on average 1 to 5 glycerol groups and in particular 1.5 to 4; the ethoxylated sorbitan fatty acid esters having from 2 to 30 moles of ethylene oxide; the sucrose fatty acid esters, the polyethylene glycol fatty acid esters, alkylpolyglycosides, derivatives of N-alkyl glucamine, oxides of amines such as oxides of alkyl ($C_{10}$-$C_{14}$) amines or oxides of N-acylaminopropylmorpholine.

(iii) Amphoteric or Zwitterionic Surfactant(s):

The amphoteric or zwitterionic surfactants, whose nature is not critical within the scope of the present invention, can notably be (non-exhaustive list) derivatives of secondary or tertiary aliphatic amines, in which the aliphatic radical is a linear or branched chain having 8 to 18 carbon atoms and containing at least one water-solubilizing anionic group (for example carboxylate, sulphonate, sulphate, phosphate or phosphonate); we may also mention the alkyl ($C_8$-$C_{20}$) betaines, the sulphobetaines, the alkyl ($C_8$-$C_{20}$) amidoalkyl ($C_1$-$C_6$) betaines or the alkyl ($C_8$-$C_{20}$) amidoalkyl ($C_1$-$C_6$) sulphobetaines.

Among the derivatives of amines, we may mention the products sold under the name MIRANOL, as described in U.S. Pat. Nos. 2,528,378 and 2,781,354 and classified in the CTFA dictionary, 3rd edition, 1982, under the designations Amphocarboxyglycinates and Amphocarboxypropionates.

These compounds are classified in the CTFA dictionary, 5th edition, 1993, under the designations Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid, Cocoamphodipropionic acid.

As an example, we may mention the cocoamphodiacetate marketed under the trade name MIRANOL® C2M concentrate by the company RHODIA CHIMIE.

(iv) Cationic Surfactants:

Among the cationic surfactants we may mention in particular (non-exhaustive list): the salts of primary, secondary or tertiary fatty amines, optionally polyoxyalkylenated; the quaternary ammonium salts such as the tetraalkylammonium, alkylamidoalkyltrialkylammonium, trialkylbenzylammonium, trialkylhydroxyalkyl-ammonium or alkylpyridinium chlorides or bromides; the imidazoline derivatives; or the oxides of amines of cationic character. Preferably the cationic surfactants have a permanent charge, i.e. have one or more quaternized nitrogen atoms.

The amounts of surfactants present in the composition to be used in the method of the invention can vary from 0.01 to 40% and preferably from 0.5 to 30% of the total weight of the composition.

The compositions applied on the keratin fibres can also comprise one or more oxidation dye precursors: one or more oxidation bases and/or one or more couplers. As examples, the oxidation bases are selected from the para-phenylenediamines, the bis-phenylalkylenediamines, the para-aminophenols, the ortho-aminophenols, the heterocyclic bases and their salts of addition.

The oxidation base or bases present are generally present in an amount ranging from about 0.001 to 20 wt. % of the total weight of the dye composition, preferably from 0.005 to 6%.

The compositions can contain one or more couplers conventionally used for the dyeing of keratin fibres. Among these couplers, we may notably mention metaphenylenediamines, metaminophenols, metadiphenols, naphthalenic couplers, heterocyclic couplers as well as their salts of addition.

The coupler or couplers are generally present in an amount ranging from about 0.001 to 20 wt. % of the total weight of the dye composition, preferably from 0.005 to 6%.

In general, the salts of addition of the oxidation bases and of the couplers for use within the scope of the invention are notably selected from the salts of addition with an acid, such as hydrochlorides, hydrobromides, sulphates, citrates, succinates, tartrates, lactates, tosylates, benzenesulphonates, phosphates and acetates and salts of addition with a base such as sodium hydroxide, potassium hydroxide, ammonia, amines or alkanolamines.

The compositions that can be used can also contain one or more additional direct dyes other than phenoxazinone derivatives of the invention and can notably be selected from the neutral, acid or cationic nitro dyes of the benzene series, the neutral, acid or cationic azo direct dyes, the neutral, acid or cationic quinone and in particular anthraquinone direct dyes, the azine direct dyes, the triarylmethane direct dyes, the indoamine direct dyes and the natural direct dyes.

The additional direct dye or dyes generally represent from about 0.001 to 20 wt. % of the total weight of the aqueous solution in which they are present, even more preferably from about 0.005 to 10 wt. %.

The pH of the composition applied on the fibres is in general between 2 and 13, preferably between 3 and 8. It can be adjusted to the desired value by means of acidifying or alkalizing agents usually employed in the dyeing of keratin fibres or else by means of conventional buffer systems.

Among the acidifying agents, we may mention as examples the inorganic or organic acids such as hydrochloric acid, orthophosphoric acid, sulphuric acid, the carboxylic acids such as acetic acid, tartaric acid, citric acid, lactic acid, and the sulphonic acids.

Among the alkalizing agents we may mention, as examples, ammonia, alkaline carbonates, alkanolamines such as mono-, di- and triethanolamines as well as their derivatives, the sodium or potassium hydroxides and compounds of the following formula (II):

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom, a $C_1$-$C_4$ alkyl or $C_1$-$C_4$ hydroxyalkyl radical.

When the composition comprises at least one oxidation dye precursor or when we wish to use direct lightening coloration, an oxidizing agent can be used.

The oxidizing agents classically used for the oxidation dyeing of keratin fibres are for example hydrogen peroxide, urea peroxide, alkali metal bromates, persalts such as perborates and persulphates, peracids and oxidase enzymes, among which we may mention peroxidases, oxidoreductases with 2 electrons such as the uricases and oxygenases with 4 electrons such as the laccases. Hydrogen peroxide is particularly preferred.

This oxidizing agent can also be present in the compositions used in the invention or can be applied separately.

The oxidizing composition can also contain various additives used classically in hair dyeing compositions and as defined previously.

According to the invention, the holding time of the compositions is in general between 1 minute and 1 hour.

The method of the invention, which consists of applying, on human hair, one or more dyes of formula (I), can be employed at a temperature varying between room temperature (20-25° C.) and 200° C., preferably between room temperature and 60° C.

The method of the invention can include a rinsing stage, or other supplementary stages such as a stage for conditioning, shaping, oxidation etc.

The examples given below serve to illustrate the invention but without limiting it in any way.

EXAMPLES

Example 1

The dye compositions 1 to 5 are prepared from the following ingredients in the proportions stated in wt. %.

|  | 1 | 2 | 3 | 4 | 5 |
|---|---|---|---|---|---|
| Benzyl alcohol | 5% | 5% | 5% | 5% | 5% |
| Benzoic acid | 0.2% | 0.2% | 0.2% | 0.2% | 0.2% |
| Ethanol | 15% | 15% | 15% | 15% | 15% |
| Hydroxyethyl cellulose | 2% | 2% | 2% | 2% | 2% |
| Dye 1 | 0.5% | | | | |
| Dye 2 | | 1% | | | |
| Dye 3 | | | 1% | | |
| Dye 4 | | | | 1% | |
| Dye 5 | | | | | 3% |
| Preservative | qs | qs | qs | qs | qs |
| Perfume | qs | qs | qs | qs | qs |
| Water | | q.s.f. 100 | q.s.f. 100 | q.s.f. 100 | q.s.f. 100 |

| | Dye | Molecular structure | Coloration obtained on hair |
|---|---|---|---|
| 1 | Resorcin blue, CAS = 71939-12-3, marketed by Acros | | Blue grey |
| 2 | Cinnabarine acid, CAS = 146-90-7 | | Red |
| 3 | Cinnabarine, CAS = 606-59-7 | | Red |
| 4 | Tramsanguine, CAS = 34083-17-5 | | Red |
| 5 | Pirenoxine sodium, CAS = 34083-17-5, marketed by THREEB-MED | | Purplish red |

The compositions are applied for 20 minutes at room temperature on a lock of natural hair with 90% of white hair and on a permed lock of hair with 90% of white hair.

After application, the locks of hair are rinsed, shampooed and dried. They are strongly coloured in red to blue and the shades obtained have low selectivity, i.e. visually the coloration obtained with the natural hair and that obtained with the permed hair are similar.

After a series of 12 washings applied on the two types of locks of hair, a slight degradation of the coloration (less than 10%) was observed.

Example 2

The following dye composition is prepared from the ingredients in the following table in the proportions stated in wt. %.

|  | 1 |
|---|---|
| Benzyl alcohol | 2.5% |
| Propylene carbonate | 10% |
| Ethanol | 5% |
| Hydroxyethyl cellulose | 2% |
| Dye 1 | 0.5% |
| Preservative | qs |
| Perfume | qs |
| Water | q.s.f. 100 |

Colouring Stage:

The composition is applied for 20 minutes at room temperature or for 45 minutes at 40° C. on a lock of natural hair with 90% of white hair and on a permed lock of hair with 90% of white hair.

After application, the locks of hair are rinsed, shampooed and dried.

The coloration of the hair is evaluated in the L*a*b* system, with a MINOLTA CM2002® spectrophotometer.

In this system, L represents the intensity: the lower the value of L*, the more intense the coloration obtained. The chromaticity is measured with the values a* and b*, a* representing the red/green axis and b* the yellow/blue axis.

Determination of the Intensity of Colouring

The coloration obtained is evaluated by measuring $\Delta E$, which is the change in colour before and after application of the coloration from the formula:

$$\Delta E = \sqrt{(L^* - L_o^*)^2 + (a^* - a_o^*)^2 + (b^* - b_o^*)^2}$$

in which L* represents the intensity, a* and b* represent the chromaticity of the coloured hair and $L_o^*$ represents the intensity and $a_o^*$ and $b_o^*$ the chromaticity of the hair before colouring. For higher $\Delta E$, the colour is more intense.

The results are presented in the following table:

|  | L | d | b* | ΔE |
|---|---|---|---|---|
| Coloured natural hair (holding time 20 minutes at room temperature) | 34.16 | 0.14 | −0.72 | 23.8 |
| Coloured natural hair (holding time 45 minutes at 40° C.) | 26.55 | 0.52 | −1.79 | 30.83 |
| Natural hair, not coloured | 53.70 | 1.84 | 12.78 |  |

Stages of Washing Resistance:

The locks of hair prepared above are submitted to a washing resistance test, which consists of carrying out 12 washings of these locks of hair with shampoo, each washing being followed by rinsing and drying.

The degradation of the colour of the locks of hair before and after the washing test is then evaluated.

This degradation is expressed as $\Delta E$.

$$\Delta E_{washing} = \sqrt{(\Delta(L_t^* - L_d^*)^2 + \Delta(a_t^* - a_d^*)^2 + \Delta(b_t^* - b_d^*)^2)}$$

in which:
$L_d^*$ represents the intensity, $a_d^*$, $b_d^*$ represent the chromaticity of the coloured hair after the washing test
$L_t^*$ represents the intensity, $a_t^*$, $b_t^*$ represent the chromaticity of the coloured hair before the washing test The percentage loss of colour is then expressed by calculating:

% loss = $\Delta E_{washing}/\Delta E \times 100$

| Lock of hair | % loss |
|---|---|
| Coloured natural hair (holding time 20 minutes at room temperature) | 7.6 |
| Coloured natural hair (holding time 45 minutes at 40° C.) | 6.7 |

These results show that the coloration obtained is only slightly degraded by the 12 repeat washings.

Stages of Light Fastness:

The coloured locks of hair are exposed to UV/visible light on half of their length for a period of 18 hours by a sun simulator with a xenon lamp producing a reproducible luminous spectrum similar to that of the sun (Suntest XLS marketed by the Atlas company). The other half of the lock of hair is masked with card.

The degradation of the colour during the test with exposure to light is then evaluated.

This degradation of colour is expressed in $\Delta E_{light}$.

$$\Delta E_{light} = \sqrt{(\Delta(L_t^* - L_d^*)^2 + \Delta(a_t^* - a_d^*)^2 + \Delta(b_t^* - b_d^*)^2)}$$

in which:
$L_d^*$ represents the intensity, $a_d^*$, $b_d^*$ represent the chromaticity of the dyed hair after the light test
$L_t^*$ represents the intensity, $a_t^*$, $b_t^*$ represent the chromaticity of the dyed hair before the light test The percentage loss is then expressed by calculating:

% loss = $\Delta E light/\Delta E \times 100$

This test of exposure to UV/visible light on the two types of locks of hair led to a slight degradation of the coloration (less than 10%).

| Lock of hair | % loss |
|---|---|
| Coloured natural hair (holding time 20 minutes at room temperature) | 4.2 |
| Coloured natural hair (holding time 45 minutes at 40° C.) | 4.5 |

These results show there is a slight degradation of colour after exposure.

The invention claimed is:

1. A composition for the coloring of keratin fibres in a medium suitable for the coloring of keratin fibres and comprising at least one dye represented by formula (1)

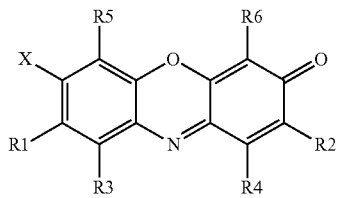

in which
- X is selected from a hydrogen atom; an alkyl radical having from 1 to 10 carbon atoms and optionally substituted with one or more hydroxyl radicals; a phenyl radical optionally substituted with one or more $C_1$-$C_{10}$ hydroxyl or alkyl radicals, a hydroxyl radical,
- R1 is selected from a hydrogen atom; a hydroxyl radical; a benzoyl or p- hydroxybenzoyl radical; a phenyl radical optionally substituted with one or more $C_1$-$C_{10}$ hydroxyl or alkyl radicals, an amino radical $NH_2$ or NHR or NRR', R and R' representing a $C_1$-$C_{10}$ alkyl or hydroxyalkyl radical, and R and R' can form, with the nitrogen atom to which they are attached, an aromatic or non-aromatic ring,
- R2 is selected from a hydroxyl radical; an amino radical $NH_2$ or NHR or NRR', R and R' being as defined previously; a phenyl radical optionally substituted with one or more $C_1$-$C_{10}$ hydroxyl or alkyl radicals,
- R3 is selected from a hydrogen atom; a hydroxyl radical; an alkyl radical having from 1 to 10 carbon atoms and optionally substituted with one or more hydroxyl radicals; a radical COR''' or COOR''' with R''' representing a hydrogen atom, a $C_1$-$C_{10}$ alkyl radical, an amino radical $NH_2$ or NHR or NRR', R and R' being as defined previously,
- R4 is selected from a hydrogen atom, a $C_2$-$C_{10}$ alkenyl radical optionally substituted with one or more hydroxyl radicals; a hydroxyl radical; a radical COOR''' or COR''' with R''' equal to hydrogen, a $C_1$-$C_{10}$ alkyl radical; an amino radical $NH_2$ or NHR or NRR', R and R' being as defined previously,
- R2 and R4 or R1 and R3 taken two at a time can together form an aromatic or non-aromatic, heterocyclic or carbocyclic ring with 5 or 6 ring members, R5 and R6 represent independently a hydrogen atom; a hydroxyl radical; an amino radical $NH_2$ and NHR or NRR', R and R' being as defined previously, and one or more surfactants or one or more thickening agents or both.

2. The composition according to claim 1, wherein the dye of formula (I) comprises $C_1$-$C_4$ alkyl radicals.

3. The composition according to claim 1 wherein the dye of formula (I) is such that R5 and R6 represent a hydrogen atom.

4. The composition according to claim 1 wherein X represents a hydrogen atom or a hydroxyl radical.

5. The composition according claim 1 wherein the dye of formula (I) is selected from:

Resorcin blue
(CAS = 71939-12-3)

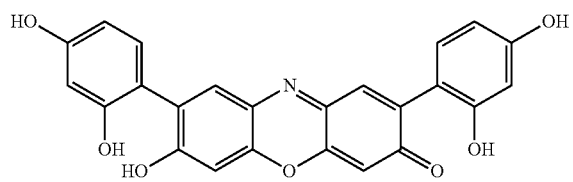

Cinnabarine acid
(CAS = 146-90-7)

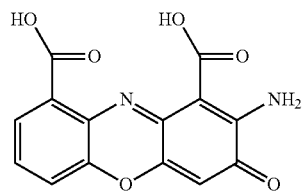

Cinnabarine
(CAS = 606-59-7)

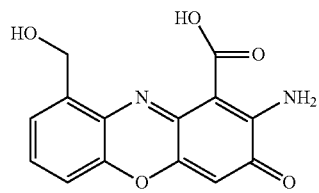

Tramsanguine,
(CAS = 34083-17-5)

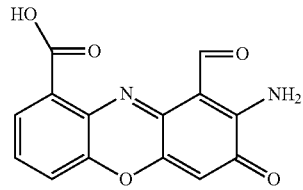

| Pirenoxine sodium, CAS = 34083-17-5 | 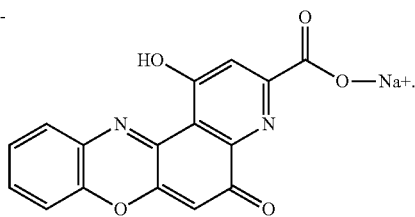 |
|---|---|

6. The composition according to claim 1 wherein the keratin fibres are hair.

7. Method of coloring of keratin fibres that comprises the application of one or more dyes of formula (I) on the fibres at least one dye represented by formula (1)

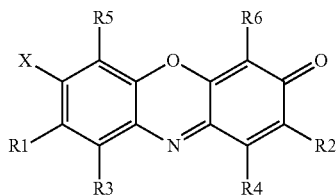

in which
X is selected from a hydrogen atom; an alkyl radical having from 1 to 10 carbon atoms and optionally substituted with one or more hydroxyl radicals; a phenyl radical optionally substituted with one or more $C_1$-$C_{10}$ hydroxyl or alkyl radicals, a hydroxyl radical, R1 is selected from a hydrogen atom; a hydroxyl radical; a benzoyl or p- hydroxybenzoyl radical; a phenyl radical optionally substituted with one or more $C_1$-$C_{10}$ hydroxyl or alkyl radicals, an amino radical $NH_2$ or NHR or NRR', R and R' representing a $C_1$-$C_{10}$ alkyl or hydroxyalkyl radical, and R and R' can form, with the nitrogen atom to which they are attached, an aromatic or non-aromatic ring, R2 is selected from a hydroxyl radical; an amino radical $NH_2$ or NHR or NRR', R and R' being as defined previously; a phenyl radical optionally substituted with one or more $C_1$-$C_{10}$ hydroxyl or alkyl radicals, R3 is selected from a hydrogen atom; a hydroxyl radical; an alkyl radical having from 1 to 10 carbon atoms and optionally substituted with one or more hydroxyl radicals; a radical COR''' or COOR''' with R''' representing a hydrogen atom, a $C_1$-$C_{10}$ alkyl radical, an amino radical $NH_2$ or NHR or NRR', R and R' being as defined previously, R4 is selected from a hydrogen atom, a $C_2$-$C_{10}$ alkenyl radical optionally substituted with one or more hydroxyl radicals; a hydroxyl radical; a radical COOR''' or COR''' with R''' equal to hydrogen, a $C_1$-$C_{10}$ alkyl radical: an amino radical $NH_2$ or NHR or NRR', R and R' being as defined previously, R2 and R4 or R1 and R3 taken two at a time can together form an aromatic or non-aromatic, heterocyclic or carbocyclic ring with 5 or 6 ring members, R5 and R6 represent independently a hydrogen atom; a hydroxyl radical; an amino radical $N_2$ and NHR or NRR', R and R' being as defined previously, for a sufficient time to obtain the desired coloration.

8. Method according to claim 7, which additionally comprises the application of an oxidizing agent mixed with the dye of formula (I) or sequentially.

9. Method of coloring according to claim 7, wherein the application of the dye of formula (I) is followed by a rinsing stage.

10. Composition according claim 1 for coloring hair, wherein the medium is suitable for the coloring of hair.

11. The composition according to claim 2, wherein the dye of formula (I) is such that R5 and R6 represent a hydrogen atom.

12. The composition according to claim 2, wherein X represents a hydrogen atom or a hydroxyl radical.

13. The composition according to claim 3, wherein X represents a hydrogen atom or a hydroxyl radical.

14. The composition according to claim 2 for coloring hair, wherein the medium is suitable for the coloring of hair.

15. The composition according to claim 3 for coloring hair, wherein the medium is suitable for the coloring of hair.

16. The composition according to claim 4 for coloring hair, wherein the medium is suitable for the coloring of hair.

17. The composition according to claim 5 for coloring hair, wherein the medium is suitable for the coloring of hair.

18. The method according to claim 7, wherein the keratin fibres are hair.

19. The method according to claim 8, wherein the keratin fibres are hair.

20. Method of coloring according to claim 8, wherein the application of the dye of formula (I) is followed by a rinsing stage.

* * * * *